United States Patent [19]

Mao et al.

[11] Patent Number: 4,665,249

[45] Date of Patent: May 12, 1987

[54] METHOD FOR FEEDING AN MTG CONVERSION REACTOR

[75] Inventors: Cheng-How Mao, Lawrenceville, N.J.; Max Schreiner, Jr., New Hope, Pa.

[73] Assignee: Mobil Oil Corporation, New York, N.Y.

[21] Appl. No.: 823,153

[22] Filed: Jan. 27, 1986

Related U.S. Application Data

[63] Continuation-in-part of Ser. No. 683,767, Dec. 19, 1984, abandoned.

[51] Int. Cl.$^4$ ............................................. C07C 1/20
[52] U.S. Cl. ........................................ 585/408; 203/14; 203/18; 203/73; 203/DIG. 9; 568/916; 585/469; 585/640; 585/733
[58] Field of Search ............... 203/18, 19, 14, DIG. 9, 203/73; 585/408, 469, 640, 733, 639; 568/916

[56] References Cited

U.S. PATENT DOCUMENTS

| | | | |
|---|---|---|---|
| 3,391,064 | 7/1968 | Akell | 203/18 |
| 3,434,937 | 3/1969 | Elliott et al. | 203/18 |
| 3,969,426 | 7/1976 | Owen et al. | 585/469 |
| 4,035,430 | 7/1977 | Dwyer et al. | 585/469 |
| 4,149,940 | 4/1979 | Pinto | 203/18 |
| 4,210,495 | 7/1980 | Pinto | 203/18 |
| 4,347,397 | 8/1982 | Dwyer et al. | 585/469 |
| 4,387,263 | 6/1983 | Vogt et al. | 585/640 |
| 4,592,806 | 6/1986 | Ilgner et al. | 203/71 |

*Primary Examiner*—Asok Pal
*Attorney, Agent, or Firm*—Alexander J. McKillop; Michael G. Gilman; L. G. Wise

[57] ABSTRACT

A method of and apparatus for reducing the amount of water in the feed to a methanol-to-gasoline (MTG) conversion reactor is described. The output products of a dehydration reactor and an aqueous methanol feed are supplied to a primary distillation tower or separator. A dimethylether (DME)/methanol mixture is taken as overhead from the primary tower and can be sent to the MTG conversion reactor to produce hydrocarbons boiling in the gasoline range. Bottoms from the primary tower, containing methanol and water, are supplied to a secondary distillation tower or separator. A methanol stream is drawn as overhead from the secondary tower and is passed to an acid catalyzed dehydration reactor where an equilibrium mixture of dimethylether, methanol, and water is produced. The equilibrium mixture is passed from the dehydration reactor to the primary distillation tower. In preferred embodiments, the conversion reactor feed from the primary distillation tower may be of a gaseous or liquid phase.

11 Claims, 5 Drawing Figures

METHOD FOR FEEDING AN MTG CONVERSION REACTOR

CROSS-REFERENCE TO RELATED APPLICATION

This is a continuation-in-part of U.S. patent application Ser. No. 683,767, filed Dec. 19, 1984, now abandoned.

BACKGROUND OF THE INVENTION

1. Field of the Invention

The present invention relates to a method and apparatus for converting methanol to gasoline (MTG). More particularly, the present invention relates to an improved method and apparatus for dewatering the feed to an MTG conversion reactor.

2. Discussion of the Prior Art

There are presently known numerous catalytic processes for the conversion of methanol to gasoline boiling range components by contacting methanol with ZSM-5 type zeolite catalyst. During the conversion process water, in the form of steam, is formed as a by-product and tends to deactivate the ZSM-5 catalyst. This steam deactivation is permanent and catalyst activity cannot be restored by regeneration. Catalyst life is influenced very strongly by the steam partial pressure and the temperature at which the reactor is operating. The amount of steam in the reactor effluent also serves to dictate the maximum temperature of the reactor operation. Consequently, the presence of water in the conversion reactor affects both the life of the ZSM-5 type catalyst and the temperature at which the reactor operates. The temperature of the reactor will influence to a certain extent the products formed and an undesirable product, durene, increases as a percentage of the output when the reactor temperature is lowered. If the durene yield could be reduced to a 2 wt.% level or lower, then dealkylation or heavy gasoline treatment (HGT) sometimes used in MTG systems can be eliminated and the product distillation unit can be simplified.

Methanol may be converted to gasoline in a two-stage operation. First, methanol is partially dehydrated, approaching an equilibrium mixture of dimethylether (DME), methanol and water in a conventional dehydration reactor. The methanol and DME are then supplied to the conversion reactor and are converted to hydrocarbon and water, which are subsequently separated out. Thus, there are three sources of water in the feed to the conversion reactor. First, there is generally 4–17 wt.% and sometimes 20 wt.% of water in the crude methanol feed, depending upon the methanol synthesis process employed upstream of the MTG system. Second, additional water is formed in the DME reactor because 2 moles of methanol converted to DME yields 1 additional mole of water. The dehydration reactor has an equilibrium range of 75–80%, and thus a large portion of water is created from the dehydration reaction. Third, water is carried by fuel gas, some of which is recycled to the conversion reactor.

FIG. 1 illustrates a conventional methanol-to-gasoline (MTG) converter in which crude methanol is supplied to dehydration reactor 10 and provides an output, which is a mixture of DME, methanol and water. The output mixture is then supplied to the conversion reactor 12, wherein it reacts over a ZSM-5 type catalyst in a known manner. The output of the conversion reactor will comprise a mixture of Liquified Petroleum Gas (LPG) and gasoline boiling range hydrocarbons, fuel gas and water which can be separated in product separator 14. A major portion of the fuel gas is recycled to the input of the conversion reactor, to control reactor temperature rise and the remainder comprising a fuel gas product.

Initially it was thought that with the FIG. 1 type MTG systems, crude methanol containing up to about 20 wt.% water content would be a satisfactory feedstock. Thus, no attempt was made to reduce water content in such a commercial MTG plant design. Although non-water removal is suitable for low water containing coal-based methanol feeds, it has been found that for other feeds it is desirable to reduce the water content of the methanol to 4 wt.% or lower. FIG. 2 illustrates the system of FIG. 1, in which a high water content crude methanol (17 wt.% H$_2$O) undergoes distillation at generally atmospheric pressure through a large diameter tower, with the distilled methanol (4 wt.% or less H$_2$O) being supplied as the input to dehydration reactor 10. This provides a minor reduction in the water content of the conversion reactor. However, as can be seen by a simple example, the water content of the crude methanol input varies only to a minor degree the water content in the feed to the conversion reactor. If a natural gas-based crude methanol with 17 wt.% water is utilized, the water in the feed to the conversion reactor is about 3.8 wt.%. For a coal-based crude methanol feed which has a 4 wt.% water content and the same recycle gas ratio, the water in the reactor feed is about 3.0 wt.%. Thus, reducing the crude methanol water content from 17 to 4 wt.% only reduces the water content of the reactor feed from 3.8 to 3.0 wt.%. After reaction in the conversion reactor, the water in the conversion reactor effluent is 7.1 and 6.4 wt.% for 17 and 4 wt.% water feeds, respectively. It would be desirable to reduce as much as possible the water content in the conversion reactor feed itself, which would serve to control the first two of the three sources of water in the reactor feed. The third source is fixed by the equilibrium condition in the product separator and is not readily controllable.

U.S. Pat. No. 4,210,495 describes a process for producing a stream of purified methanol which includes feeding a water-methanol mixture containing small quantities of ethanol, ketones, and higher alcohols to a first distillation column. Product methanol is withdrawn from the upper level of the first column, and a sidestream of aqueous methanol is directed from the first column to a second distillation column. A second product stream of methanol is obtained from the upper level of the second column. The first distillation column is operated at low pressure (6.9–137.4 kPa) and the second distillation column is operated at the same low pressure or at a pressure moderately higher (137.4–824.5 kPa higher) than the first column. The process discussed herein calls for the operation of a first distillation column at a substantially higher pressure (825–2040 kPa), giving a product stream of dimethylether and methanol wherein the molar ratio of DME to methanol is much greater than unity. Such a stream containing a significant amount of dimethylether is excellent feedstock for a methanol-to-gasoline conversion unit.

It is an object of the present invention to provide a method and apparatus for reducing the water content of the feed to a conversion reactor in an MTG plant.

It is a further object of the present invention to provide a method and apparatus for increasing catalyst life in a conversion reactor and/or operating the conversion reactor at either a higher temperature or at a lower recycle gas ratio, with the benefits resultant therefrom.

SUMMARY OF THE INVENTION

The above and other objects are achieved in accordance with the present invention by methods and means for: passing a crude methanol feed containing a minor amount of water to an upperstage of a primary distillation tower; conducting a dehydration reaction product of dimethylether, methanol, and water from a dehydration reactor to an intermediate stage of the distillation tower; withdrawing from the primary distillation tower an overhead stream of an essentially water-free dimethylether-containing feedstream having a dimethylether to methanol molar ratio of at least about 1.5 1; withdrawing from the primary distillation tower a bottoms stream of aqueous methanol; conducting the bottoms stream containing the aqueous methanol to a secondary distillation tower; withdrawing from the secondary distillation tower an overhead methanol stream and a bottoms stream of water which is recovered in a collection zone; passing the overhead stream of methanol to a dehydration reactor; and withdrawing from the dehydration reactor a reaction product of dimethylether, methanol, and water, which reaction product is recycled to the primary distillation tower.

The essentially water-free dimethylether containing primary tower overhead stream is preferably sent diretly to a methanol-to-gasoline (MTG) conversion reactor containing a ZSM-5 type catalyst. Advantageously, the primary distillation tower is operated at a pressure similar to that of the MTG conversion reactor. Ordinarily, the primary distillation tower is operated at a pressure of about 825 to 2040 kPa.

BRIEF DESCRIPTION OF THE DRAWINGS

A more complete appreciation of the invention, and many of the attendant advantages thereof, will be readily apparent as the same becomes better understood by reference to the accompanying drawings, wherein.

DETAILED DESCRIPTION OF THE PREFERRED EMBODIMENTS

Figure 3:
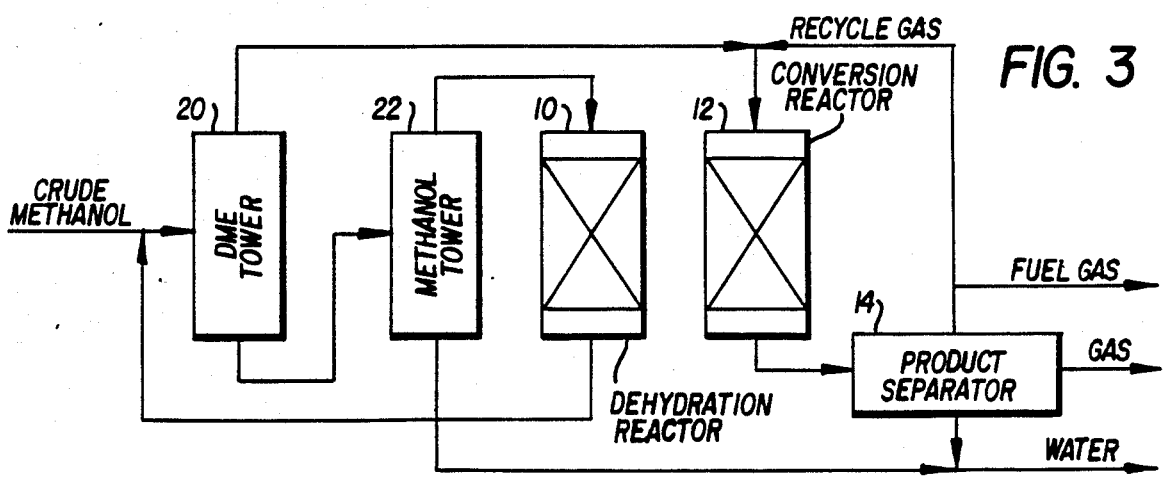
FIG. 3 is a block diagram illustrating the present invention, as applied to an MTG system.

Referring now more particularly to the drawings, wherein like numerals represent like elements throughout the several views, FIG. 3 is a block diagram illustrating one embodiment of the present invention. The output of the dehydration reactor 10, instead of providing the feed to the conversion reactor 12 as in the prior art, is supplied to a DME tower 20 concurrently with the crude methanol input. The overhead from the DME or primary distillation tower will be a mixture of DME and methanol, wherein the DME concentration ranges from pure DME to a DME/methanol mixture having the same ratio as the output of a conventional dehydration reactor effluent, both of which may have up to approximately 1 mole percent of water included. The molar ratio of DME to methanol in the overhead stream from the primary distillation tower is usually in the range from 1.15:1 to 99:1, with a water content of about 1 mole percent. A change in the DME/methanol ratio in the conversion reactor feed, especially or a ZSM-5 type catalyst, may result in an alteration of the reaction path. DME may be less reactive than methanol for benzene alkylation to form durene (1,2,4,5-tetra-methyl-benzene). With a pure DME feed, the least amount of oxygen will be converted into water in the conversion reactor.

The primary distillation tower or first separation zone preferably contains at least twenty theoretical stages. The crude methanol feed is directed to an upper stage of the tower which is from two to five stages above the intermediate stage inlet for the reaction product mixture of dimethylether, methanol, and water. The primary distillation tower or first separation zone is, in a preferred embodiment, operated at a reflux ratio of 1.1 to 3.8.

The bottoms of the DME tower 20, containing a mixture of methanol and water, are sent to a methanol tower or secondary distillation tower 22, where the mixture is separated into an overhead methanol output and a bottoms water output. The overhead from the methanol tower actually contains about 17 wt.% of water, which is subsequently fed in a continuous manner to the dehydration reactor 10 which contains an acid dehydration cataylst such as gamma alumina. The water in the overhead product eases the tower operation and enables the distillation to be carried out under pressure. The bottoms of the methanol tower or second separation zone 22 comprise primarily water which, in conjunction with water from the product separator 14, are removed off site for treatment.

Figure 1:
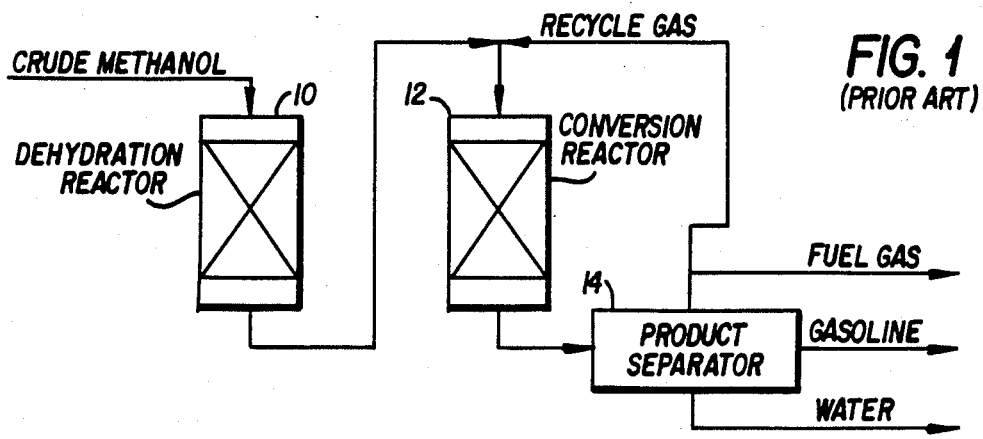
FIG. 1 is a block diagram illustrating a conventional prior art MTG system with no water reduction in the conversion reactor feed.
Figure 2:
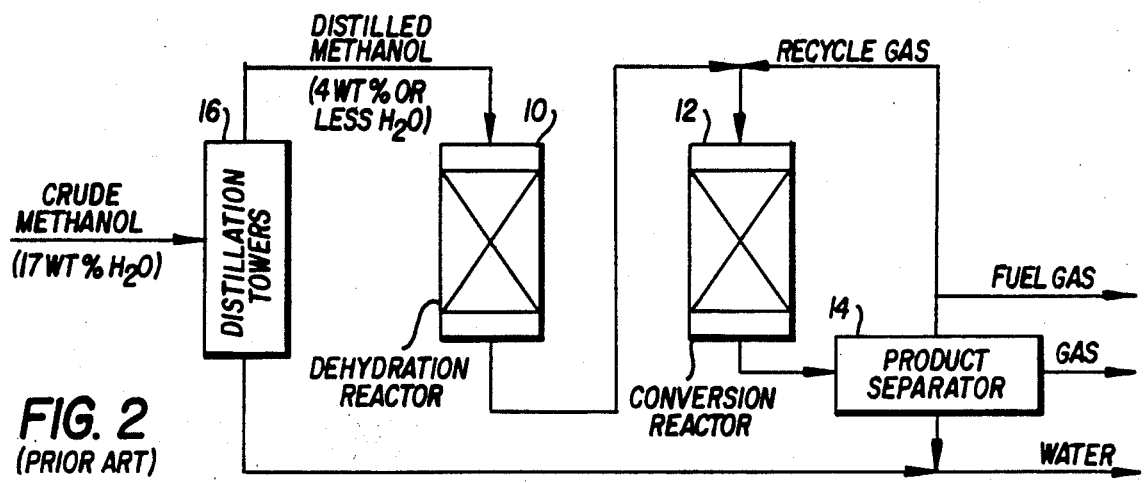
FIG. 2 is a block diagram of a conventional prior art MTG system with distillation towers supplying reduced water content methanol as a feed to the MTG conversion reactor.

Whereas the FIG. 1 and FIG. 2 conversion reactor feeds contained water in the amount of 17 and 4 wt.%, respectively, in accordance with the FIG. 3 operation the reactor feed would have about 0.4 wt.% of water. It should also be noted that 90% of this 0.4 wt.% water in the conversion reactor feed in FIG. 3 comes from the recycle gas. This is a substantial reduction in the amount of water in contact with the ZSM-5 catalyst, increasing the catalyst life and providing other potential process benefits. In addition to an increase in catalyst life, the temperature, pressure and space velocity operating range will be enlarged, allowed greater freedom in optimum plant design. For example, the recycle gas ratio may be reduced to provide the same partial pressure of water, giving a constant catalyst life but reducing the recycle gas compressor horsepower requirement. If the water partial pressure is lowered, the reactor may be operated at a higher temperature, reducing the durene yield. If durene yield can be reduced to the 2 wt.% level or below, then a heavy gasoline treater (HGT) unit (not shown), utilized in most commercial MTG plants, can be eliminated and the product distillation unit can be simplified, reducing the capital investment in such a plant.

Figure 4:
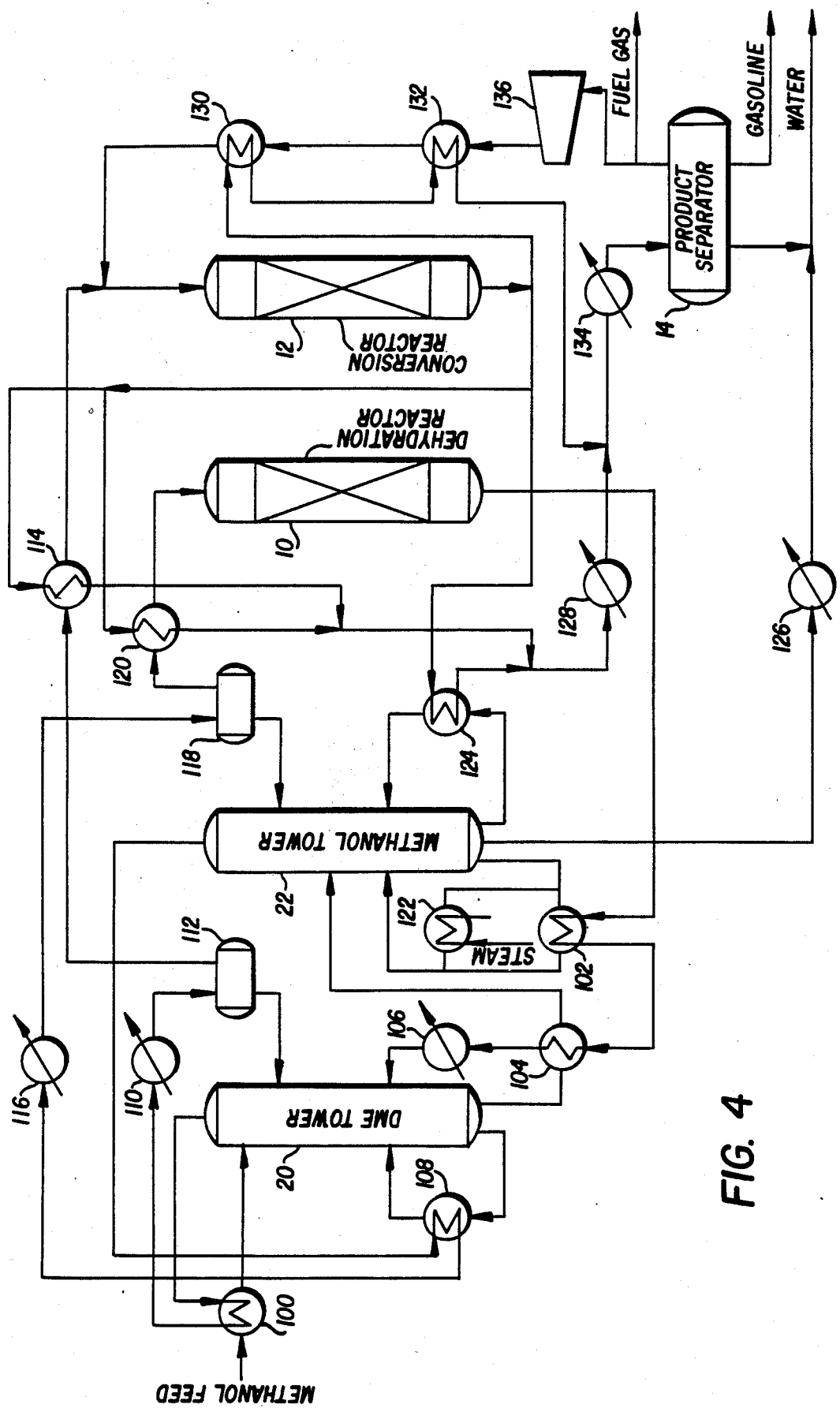
FIG. 4 is a process flow diagram of a preferred embodiment of the present invention, illustrating a vapor phase feed to the conversion reactor.

FIG. 4 illustrates a process flow diagram in accordance with the present invention, with a vapor phase feed to the conversion reactor system. Crude methanol at approximately 100° F. at a feed rate of around 12,582 lb.moles/hour is supplied to heat exchanger 100 in which about 67.9M (millions of BTU's per hour) are added, raising the temperature to around 265° F. The heated crude methanol is supplied to the DME tower 20, along with the reaction products from the dehydration reactor 10. The dehydration reactor products (DME, methanol, water) leave the dehydration reactor at approximately 290 psia and 760° F. and pass through reboiler 102, exchanging about 74.3M with the bottoms from methanol tower 22, which are being reboiled. The dehydration reactor products pass through a further heat exchanger 104, serving to heat the bottom products of the DME tower with a heat flow of around 18M. After additional cooling in cooler 106, which removes about 5.3M, the dehydration reactor products at around 359° F. are combined with the crude methanol feed in the DME tower 20. The DME tower bottoms are heated in reboiler 108 from an entry temperature of approximately 349° F. to an exit temperature of around 353° F., with a heat exchange of about 131M. The DME tower overheads leave at about 300° F., heating the input crude methanol in heat exchanger 100 and cooling the overheads to around 293° F. which then are further cooled in cooler 110 which removes approximately 181M. The resultant cooled vapors are supplied to separator 112 at around 265 psia and any liquid condensate is resubmitted to the DME tower 20. However, vapor phase products from separator 112 are supplied to heat exchanger 114 which, through the addition of about 79.4M, raises the temperature from around 259° to about 750° F., whereupon the products are mixed with a recycled gas stream at approximately 651° F. and the combination comprises the input feed to the conversion reactor 12 at around 667° F. and 236 psia.

The DME tower bottoms, comprising primarily methanol and water, are supplied to methanol tower 22 at about 370° F. The methanol tower overheads are circulated through reboiler 108, with around 131M being removed to lower the temperature to approximately 369° F., whereupon they are further cooled in cooler 116 which removes around 42.9M and passes the cooled methanol overheads to separator 116 at about 350 psia. Condensate in the separator is resubmitted to the methanol tower 22 and the vapor phase, at approximately 366° F., is further heated in heat exchanger 120 by the addition of around 49M and submitted to the dehydration reactor 10 at approximately 600° F. and 330 psia.

The methanol tower bottoms are reheated in reboiler 102, as previously discussed, in a steam powered reboiler by the addition of around 212.1M and by further reboiler 124, with the addition of about 99.8M, and resubmitted to the methanol tower at approximately 436° F. The methanol tower bottoms comprising primarily water, which is not recirculated and reboiled, is cooled from around 436° F. by cooler 126, which removes approximately 58.6M and the resultant water is removed for off site treatment.

The conversion reactor bottoms at around 206 psia and 804° F. are split, with a portion providing heat for heat exchanger 114, heat exchanger 120 and reboiler 124. The conversion reactor products, after losing heat in heaters 114, 120 and reboiler 124, are passed into cooler 128 at about 455° F., where approximately 105M is removed, reducing the temperature to around 213° F. on exit.

The other portion of the conversion reactor stream serves to heat the recycle gas in heat exchangers 130 and 132 and then rejoins the output of cooler 128 at a temperature of about 193° F. The reunited conversion reactor product streams combine at a temperature of around 198° F. and are further cooled in cooler 134, which removes approximately 257.5M and supplies the conversion reactor products to the product separator 14 at around 199 psia and 100° F. At this temperature and pressure, raw gas can be an additional product output and is separated from water contained in the reaction products in the normal manner.

The vaporous products in the product separator 14 may be removed at about 198 psia as fuel gas, but the majority is compressed in the recycle compressor 136 from 198 to around 268 psia and a temperature of approximately 155° F., requiring about 22,200 hp for the compression. The compressed recycle gas is heated in heater 132 by the addition of around 50.5M, raising its temperature to about 197° F. The compressed and heated recycle gas is further heated in heater 130 by the addition of approximately 650M to a final temperature of around 657° F., where it is resubmitted to the conversion reactor 12.

Thus, it can be seen that in the above process flow diagram a substantially vaporous phase feed can be provided to the conversion reactor and a relatively efficient use of heat can be maintained, requiring little energy input other than that required by the recycle compressor.

Figure 5:
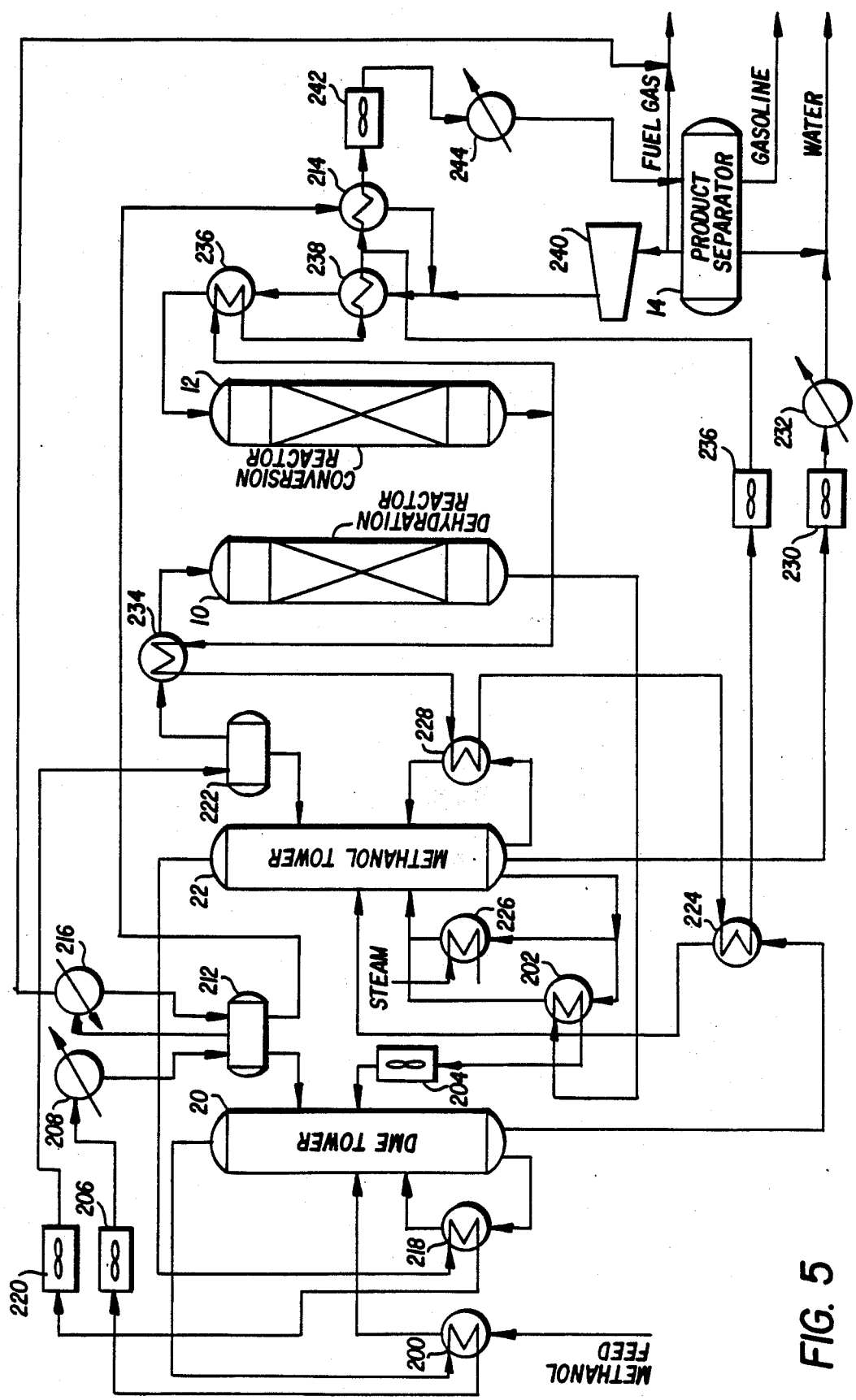
FIG. 5 is a process flow diagram of a preferred embodiment of the present invention, illustrating a liquid phase feed to the conversion reactor.

FIG. 5 illustrates a similar process flow diagram for a methanol-to-gas conversion plant in accordance with the present invention, but uitlizing a liquid phase feed to the conversion reactor system. As in FIG. 4, the input 12,582 lb.moles/hour of crude methanol at around 100° F. is supplied through heat exchanger 200, adding 74.7M, raising its temperature to approximately 185° F. upon entrance to the DME tower 20. The bottoms output of the dehydration reactor 10 at about 170 psia and around 760° F. supplies aproximately 82.8M to reboiler 202 and enters air fin cooler 204 at around 420° F. The air fin cooler removes about 22.7M, allowing the dehydration reactor bottoms product to be supplied to the DME tower at around 327° F.

The DME tower overhead is at approximately 160 psia and 226° F. and suplies the heat product to heat exchanger 200 and is then supplied to air fin cooler 206 and liquid cooler 208, which together remove around 261.3M before the products pass to separator 212 at about 100° F. and 150 psia. A portion of the liquid in the separator 212 is returned to the DME tower and another portion is supplied at around 100° F. to heat exchanger 214, which adds approximately 117.4M to vaporize the liquid product. The gaseous phase component is recirculated through cooler 216 which condenses DME and provides a fuel gas product which is removed from the system.

The DME tower bottoms leave at around 305° F., have about 121.3M added in reboiler 218 and are resubmitted to the DME tower 20 at approximately 310° F. Reboiler 218 is heated by the overhead products leaving methanol tower 22 at around 245 psia and 341° F., which pass through the reboiler through air fin cooler 220, which removes about 6M before finally being supplied to separator 222 at around 235 psia. The DME tower bottoms which are not reboiled leave the tower at about 310° F. and 165 psia, have approximately 34.4M added in heat exchanger 224 and are introduced at around 358° F. to methanol tower 22. The methanol tower bottoms are reboiled in previously discussed reboiler 202 and additional reboilers 226 and 228. The bottoms input to steam powered reboiler 226 are at around 401° F. and, after the input of approximately 162.2M, reenter the methanol tower at about 402° F. The bottoms input to reboiler 228 has about 104.8M added to it before resubmission to the methanol tower 22. The non-reboiled bottoms products leave the methanol tower at around 250 psia and about 402° F., pass through air fin cooler 230 which removes approximately 44.4M and drops the temperature to around 140° F, and pass through liquid cooler 232 which removes about 6.8M, reducing the temperature to around 100° F. for withdrawal from the system.

The gaseous phase, primarily methanol vapor, from separator 222 at around 334° F., passes into heat exchanger 234 which adds about 63.9M, raising the temperature to approximately 600° F. and supplies the dehydration reactor 10 as an input at around 220 psia. The output of the dehydration reactor will be at about 170 psia and 760° F., and serves to provide heat to reboiler 202 before it is submitted to the DME tower, as previously noted.

The output of the conversion reactor 12 is at around 292 psia and 791° F. and is split into two streams. The first stream supplies heat to heat exchanger 234 and then reboiler 228 and heat exchanger 224, supplying heat to these heat exchangers as previously noted, until its temperature has been reduced to about 344° F. The first stream is then cooled in air fin cooler 236, where approximately 51.2M is removed, reducing the temperature to around 231.8° F. The other stream of the conversion reactor output provides heat to heat exchangers 236 and 238, whereupon it rejoins the first stream and serves to heat the liquid phase material in heat exchanger 214.

The vaporous products in product separator 14 at about 263 psia and 100° F. is partially removed as fuel gas, with the remainder being recompressed in an approximately 13,800 hp compressor 240. The vapor output from the compressor at around 139° F. and the heated vapor output of heat exchanger 214 combine at about 159° F. as an input to heat exchanger 238. The temperature of the vapor stream is raised to about 215.8° F. and, with the addition of approximately 571.5M in heat exchanger 236, is supplied at around 316 psia to the conversion reactor 12 at about 630° F. The conversion reactor output second stream enters heat exchanger 238 and is cooled to about 201° F., whereupon it is combined with the first stream at around 231.8° F. for a resultant stream temperature of approximately 211° F., which passes through heat exchanger 214 and into air fin cooler 242. The air fin cooler removes around 53.8M, reducing the temperature to about 140° F., and supplies the stream to liquid cooler 244 which removes an additional 74.5M, dropping the product temperature to around 100° F. where it is provided to product separator 14.

Thus in the above specific embodiments it can be seen that the liquid or vaporous feed can be supplied to the conversion reactor with a less than 1 wt.% of water. This results in less steam in the reactor with consequent increases in catalyst life or changes in the operating cycle which permit reduced durene yield and other benefits.

In view of the above disclosure, many modifications and variations on this feed dewatering system will become obvious to those of ordinary skill in the art. Depending on the desirability of various output products, the feed to the conversion reactor can be varied from pure DME to a DME/methanol mixture ratio, which ratio would be that normally expected as the output of the dehydration reactor. If the partial pressure of water can be reduced in the conversion reactor, the horsepower requirements of the recycle compressor can be reduced. If it is desirable to increase the life of the catalyst, then a higher recycle gas ratio may be utilized with a lower partial pressure of water. Depending on the desirability of durene in the output product, the conversion reactor may be operated at a higher temperature due to the lower water partial pressure. If durene yield is reduced sufficiently, then the HGT unit can be eliminated, simplifying current commercial MTG plant design. Therefore, the present invention is not limited by the above disclosure and is limited only by the scope of the claims attached hereto.

The invention in any of the above embodiments can be configured as an original installation or adapted as a retrofit to an existing methanol-to-gas (MTG) system.

What is claimed is:

1. A continuous process for producing an essentially water-free dimethylether-containing feedstream comprising:
    passing a crude methanol feed containing a minor amount of water to an upper stage of a pressurized primary distillation tower and concurrently passing a dehydration reaction product of dimethylether, methanol, and water from a dehydration reactor to an intermediate stage of the primary distillation tower;
    withdrawing from the primary distillation tower an overhead stream of an essentially water-free dimethylether-containing feedstream having a dimethylether to methanol molar ratio of at least about 1.15 to 1 and an aqueous methanol bottoms stream;
    conducting the bottoms stream containing aqueous methanol to a secondary distillation tower;
    withdrawing from the secondary distillation tower an overhead methanol stream and a bottoms stream of water which is recovered in a collection zone;
    passing the secondary overhead methanol stream to a dehydration reactor containing an acid methanol dehydration catalyst; and
    withdrawing from the dehydration reactor a dehydration reaction product stream of dimethylether, methanol, and water, which reaction product stream is recycled to the primary distillation tower.

2. The process of claim 1 wherein the overhead stream of an essentially water-free dimethylether-containing feedstream from the primary distillation tower is sent directly to a methanol-to-gasoline conversion reactor containing ZSM-5 catalyst.

3. The process of claim 2 wherein the primary distillation tower is operated at a minimum pressure of at least that of the methanol-to-gasoline conversion reactor.

4. The process of claim 1 wherein the primary distillation tower is operated at a pressure of about 825 to 2040 kPa.

5. A process according to claim 1 wherein the primary distillation tower contains at least twenty theoretical stages.

6. A process according to claim 5 wherein the crude methanol feed enters the primary distillation tower at an upper inlet which is at least two theoretical stages above the intermediate inlet for the reaction product mixture of dimethylether, methanol, and water.

7. A process according to claim 1 wherein the primary distillation tower is operated at a reflux ratio of 1.1 to 3.8.

8. A process according to claim 1 wherein the overhead from the primary distillation tower has a dimethylether to methanol molar ratio of from 1.5:1 to 99:1 and a water content not more than about 1 mole percent.

9. A process according to claim 1 wherein the crude methanol feed contains about 4 to 20 wt. percent water.

10. A continuous method for converting a methanol feedstream to a substantially dewatered mixture consisting essentially of dimethylether and methanol, comprising the steps of
  distilling the methanol feedstream in a first separation zone concurrently with dehydration reaction effluent to provide an ether rich first overhead stream substantially free of water and an aqueous methanol first liquid bottoms stream;
  further distilling the aqeuous methanol stream in a second separation zone to provide a methanol-rich second overhead stream and a second liquid bottoms stream predominately comprising water;
  contacting the methanol-rich second overhead stream with an acid dehydration catalyst in a dehydration reaction zone at elevated temperature to convert methanol to dimethylether and water; and
  passing the dehydration reaction effluent to the first separation zone.

11. A continuous process for producing an essentially water-free dimethylether-containing feedstream for a chemical conversion reactor comprising:
  passing a crude methanol feed containing a minor amount of water to an upper stage of a pressurized primary distillation tower operated at a minimum pressure of at least that of the chemical conversion reactor and concurrently passing a dehydration reaction product of dimethylether, methanol, and water from a dehydration reactor to an intermediate stage of the primary distillation tower;
  withdrawing from the primary distillation tower an overhead stream of an essentially water-free dimethylether-containing feedstream having a dimethylether to methanol molar ratio of at least about 1.15 to 1 and an aqueous methanol bottoms stream;
  conducting the overhead stream of the dimethylether-containing feedstream from the primary distillation tower to a chemical conversion reactor;
  conducting the bottoms stream containing aqueous methanol to a secondary distillation tower;
  withdrawing from the secondary distillation tower an overhead methanol stream and a bottoms stream of water which is recovered in a collection zone;
  passing the secondary overhead methanol stream to a dehydration reactor containing an acid methanol dehydration catalyst; and
  withdrawing from the dehydration reactor a dehydration reaction product stream of dimethylether, methanol, and water, which reaction product stream is recycled to the primary distillation tower.

* * * * *